US012691194B2

(12) United States Patent
Pollock

(10) Patent No.: US 12,691,194 B2
(45) Date of Patent: Jul. 28, 2026

(54) UNIT DOSE PACK FOR CLEANING SURGICAL INSTRUMENTS

(71) Applicant: Boston Scientific Scimed, Inc., Maple Grove, MN (US)

(72) Inventor: Ryan Vincent William Pollock, Leominster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 509 days.

(21) Appl. No.: 18/320,386

(22) Filed: May 19, 2023

(65) Prior Publication Data

US 2023/0372564 A1     Nov. 23, 2023

Related U.S. Application Data

(60) Provisional application No. 63/343,956, filed on May 19, 2022.

(51) Int. Cl.
| | |
|---|---|
| *C09K 3/22* | (2006.01) |
| *A61L 2/18* | (2006.01) |
| *A61L 2/24* | (2006.01) |
| *C11D 17/00* | (2006.01) |
| *A61L 103/15* | (2026.01) |

(52) U.S. Cl.
CPC .................... *A61L 2/18* (2013.01); *A61L 2/24* (2013.01); *A61L 2103/15* (2026.01); *A61L 2202/17* (2013.01)

(58) Field of Classification Search
CPC .......... A61L 2/18; A61L 2/24; A61L 2202/17; A61L 2202/24; A61B 90/70; C11D 17/045; C11D 3/2093; C11D 11/00; C11D 3/48; C02F 1/68

USPC .............................. 422/28; 252/102; 510/441
See application file for complete search history.

(56) References Cited

U.S. PATENT DOCUMENTS

| | | | |
|---|---|---|---|
| 3,630,920 | A | 12/1971 | Freifeld et al. |
| 4,578,200 | A | 3/1986 | Burckett St. Laurent et al. |
| 5,589,267 | A | 12/1996 | Delwel et al. |
| 5,900,395 | A | 5/1999 | Nicholson et al. |
| 6,340,664 | B1 | 1/2002 | Gassenmeier et al. |
| 2003/0165691 | A1 | 9/2003 | Smith et al. |
| 2006/0122088 | A1 | 6/2006 | Sadlowski et al. |

(Continued)

OTHER PUBLICATIONS

International Search Report and Written Opinion dated Aug. 21, 2023 for International Application No. PCT/US2023/022848.

*Primary Examiner* — Monzer R Chorbaji
(74) *Attorney, Agent, or Firm* — Seager, Tufte & Wickhem, LLP

(57)     ABSTRACT

In some embodiments, the present disclosure pertains to a unit dose pack for forming a bath for cleaning medical instruments. The unit dose pack may comprise at least a first chamber that contains an enzymatic detergent composition comprising one or more enzymes, the first chamber being formed from at least one first sheet of material that comprises a water-soluble film, and the at least one first sheet of material encapsulating the enzymatic detergent composition, wherein upon immersion in water, the enzymatic detergent composition is released from the first chamber into the water. In other embodiments, the present disclosure pertains to a method of cleaning a medical instrument using at least one such unit dose pack. In some embodiments, the medical instrument is an endoscope.

18 Claims, 2 Drawing Sheets

(56)            References Cited

U.S. PATENT DOCUMENTS

| | | | |
|---|---|---|---|
| 2013/0284637 A1* | 10/2013 | Chou | C11D 3/2093 |
| | | | 206/568 |
| 2014/0054831 A1 | 2/2014 | Emerson et al. | |
| 2018/0066208 A1 | 3/2018 | Olson et al. | |
| 2019/0218486 A1 | 7/2019 | Oberwalder | |
| 2020/0131457 A1 | 4/2020 | Depoot et al. | |

\* cited by examiner

UNIT DOSE PACK FOR CLEANING SURGICAL INSTRUMENTS

CROSS-REFERENCE TO RELATED APPLICATIONS

This application claims the benefit of U.S. Provisional Patent Application Ser. No. 63/343,956 filed on May 19, 2022, the disclosure of which is incorporated herein by reference.

TECHNICAL FIELD

The present disclosure relates to unit dose packs that are useful for cleaning and disinfecting surgical instruments such as endoscopes and the like.

BACKGROUND OF THE INVENTION

An endoscope is an elongate cylindrical instrument, which may be rigid or flexible and which incorporates an optical or video system and a light source. The endoscope is configured such that one end can be inserted to some depth into a body cavity or surgical incision so that surfaces at or near the internally inserted end of the endoscope can be viewed by an external observer.

During a procedure, a reusable endoscope may be exposed to biological material from the patient, for example, mucous, saliva, feces, blood, tissue, etc. After an endoscopic procedure is completed, the endoscope must be cleaned and disinfected/sterilized prior to reuse on another patient. To this end, used endoscopes are subjected to a pre-cleaning process (known as "reprocessing") prior to disinfection or sterilization. Disinfection or sterilization of an instrument which has not been thoroughly pre-cleaned may lead to patient infections.

Conventionally, during reprocessing, detergent is dosed into a sink or receptacle where it is mixed by the filling water and the endoscope is immersed into the bath of this water. Sometimes, standard sized reprocessing sinks are employed, which results in more consistent fill levels, however there may be inconsistencies in available equipment at reprocessing facilities. Additionally, filling water dilutes the detergent and may introduce variables based on the water quality of the water coming into the building, which may affect the effectiveness of the detergent solution to clean the endoscope.

Detergent dosing is another aspect of reprocessing an endoscope. Under-dosing the detergent may result in insufficient cleaning. Over-dosing the detergent can result in prolonged rinsing stages or residue remaining inside the scope, which can compromise effective clinical outcomes. Proper dilution of detergent used during reprocessing is therefore important to efficient, economical cleaning and good cleaning results.

Current dosing methods include hand pumps and constant dosing pumps. However, the results of these dosing methods vary. Dosing pumps require maintenance and calibration, whereas hand pumps are wildly user-dependent for proper dosing. In addition, the user may use less exact measurements, with an associated likelihood of under-dosing or over-dosing the detergent.

A more robust solution is desired to create a more manageable detergent dosing while potentially addressing other factors to maintain the detergent's effectiveness.

SUMMARY

In some embodiments, the present disclosure pertains to a unit dose pack for forming a bath for cleaning medical instruments. The unit dose pack may comprise at least a first chamber that contains an enzymatic detergent composition comprising one or more enzymes, the first chamber being formed from at least one first sheet of material that comprises a water-soluble film, and the at least one first sheet of material encapsulating the enzymatic detergent composition, wherein upon immersion in water, the enzymatic detergent composition is released from the first chamber into the water.

In some embodiments, the enzymatic detergent composition may be a liquid composition, a gel composition, a powder composition, or a combination thereof.

In some embodiments, which can be used in conjunction with any of the above embodiments, the enzymatic detergent composition comprises a protease enzyme and/or an amylase enzyme.

In some embodiments, which can be used in conjunction with any of the above embodiments, the water-soluble film is a water-soluble polymer film.

In some embodiments, which can be used in conjunction with any of the above embodiments, the first sheet of material further comprises a water-resistant barrier layer disposed between the water-soluble film and the enzymatic detergent composition. In some of these embodiments, the water-resistant barrier layer is sufficiently thin such that after the water-soluble film dissolves upon immersion in water, the water-resistant barrier layer tears with gentle agitation thereby releasing the enzymatic detergent composition.

In some embodiments, which can be used in conjunction with any of the above embodiments, the unit dose pack further comprises a second chamber that is separate from the first chamber and contains a water treatment composition, the second chamber being formed from at least one second sheet of material that comprises a water-soluble film, and the at least one second sheet of material encapsulating the water treatment composition.

In some of these embodiments, the at least one first sheet of material and the at least one second sheet of material are the same, and the enzymatic detergent composition and the water treatment composition are released at substantially the same time upon immersion in water.

In some of these embodiments, the at least one first sheet of material and the at least one second sheet of material are different, and the water treatment composition is released before the enzymatic detergent composition upon immersion in water. For example, a thickness of the water-soluble film in the at least one first sheet of material may be greater than a thickness of the water-soluble film in the at least one second sheet of material and/or the water-soluble film in the at least one second sheet of material may have a greater water solubility than a water solubility of the water-soluble film in the at least one first sheet of material.

In some embodiments, which can be used in conjunction with the above embodiments, the water treatment composition is selected from a disinfectant, an anti-disinfectant, a water softener, a water hardener, or a pH modifier.

In some embodiments, which can be used in conjunction with the above embodiments, the unit dose pack further comprises a third chamber that is separate from the first chamber and the second chamber, wherein the third chamber contains an additional treatment composition, wherein the third chamber is formed from at least one third sheet of material that comprises a water-soluble film, and wherein the at least one third sheet of material encapsulates the additional treatment composition. In some of these embodiments, the water treatment composition is a water disinfectant composition, and the additional treatment composition is an anti-disinfectant composition. Upon immersion in water, the water treatment composition is released prior to the additional treatment composition, and the additional treatment composition is released prior to release of the enzymatic detergent composition.

In some embodiments, the present disclosure pertains to a unit dose pack for forming a bath for cleaning medical instruments, with the unit dose pack comprising (a) a first chamber that contains an enzymatic detergent composition that comprises a protease enzyme and amylase enzyme, the first chamber being formed from at least one first sheet of material that comprises a water-soluble polymer film and the at least one first sheet of material encapsulating the enzymatic detergent composition and (b) a second chamber that is separate from the first chamber and contains a water treatment composition, the second chamber being formed from at least one second sheet of material that comprises a water-soluble polymer film and the at least one second sheet of material encapsulating the water treatment composition.

In some embodiments, the at least one first sheet of material and the at least one second sheet of material are different and the water treatment composition is released before the enzymatic detergent composition upon immersion in water.

In some of these embodiments, a thickness of the water-soluble polymer film in the at least one first sheet of material is greater than a thickness of the water-soluble polymer film in the at least one second sheet of material.

In other embodiments, the present disclosure pertains to a method of cleaning a medical instrument that comprises (a) forming a bath by filling a sink with a predetermined volume of filling water and adding at least one-unit dose pack in accordance with any of the above embodiments to the filling water and (b) cleaning the medical instrument by a method comprising immersing the medical instrument in the bath.

In some embodiments, the medical instrument is an endoscope.

BRIEF DESCRIPTION OF THE DRAWINGS

The accompanying drawings, which are incorporated in and constitute a part of this specification, schematically illustrate various exemplary embodiments and together with the description serve to explain the principles of the present disclosure.

DETAILED DESCRIPTION

The present disclosure is directed to the delivery of enzymatic detergent in the form of standardized unit-dose packs, which may also be referred to as pods or pouches. The unit dose packs are used to form a bath for cleaning surgical instruments including endoscopes such as colonoscopes, duodenoscopes, and bronchoscopes, among others. As one specific example, a colonoscope is used for diagnostic and surgical procedures of the human colon. The colon insertion portion of the instrument is approximately 2 meters long and has one or more hollow channels, or lumens. These lumens run the length of the endoscope. The lumens allow for gas to be injected into the colon to inflate the organ, they enable liquids to be injected for irrigation or lens washing, they allow liquids to be aspirated, and they allow long flexible instruments to be inserted to allow biopsies to be taken and bleeding to be stopped.

In the present disclosure, the cleaning bath may be formed by adding one or more of the standardized unit dose packs to filling water in a cleaning sink having a standardized volume to form the bath. By filling the sink to a predetermined level and by adding the correct number of unit-dose packs (e.g., one, two, three, four, etc., depending on sink volume and desired concentration), the user can be assured that the proper dose of detergent has been applied to the bath.

Figures 1, 2, 3:
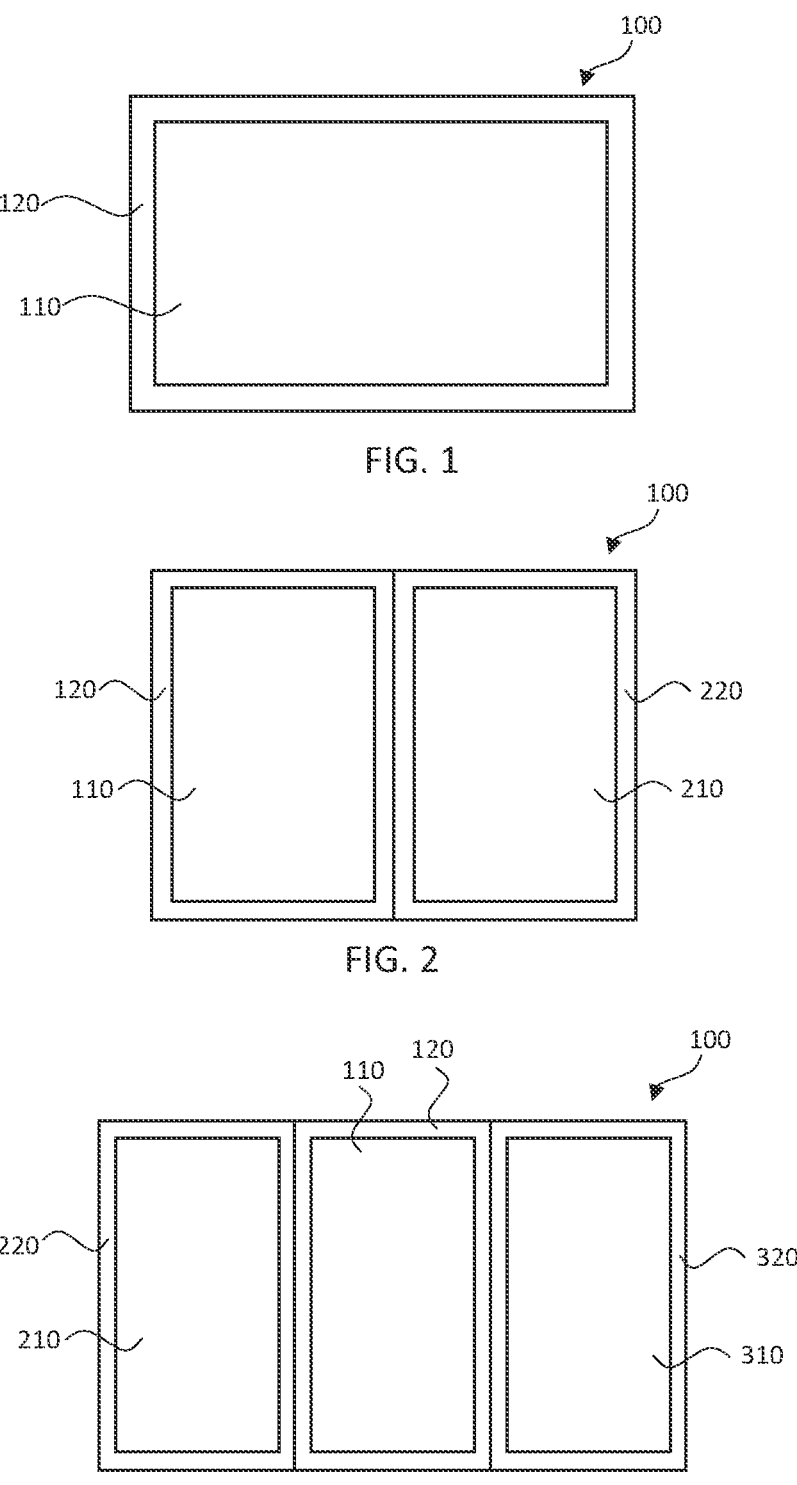
FIG. 1 schematically depicts a unit dose pack, in accordance with an embodiment of the present disclosure.
FIG. 2 schematically depicts a unit dose pack, in accordance with another embodiment of the present disclosure.
FIG. 3 schematically depicts a unit dose pack, in accordance with a further embodiment of the present disclosure.

With reference now to the schematic illustration of FIG. 1, the unit dose packs 100 of the present disclosure comprise at least a first chamber 110 that contains an enzymatic detergent composition. In various embodiments, the first chamber is formed from at least one first sheet of material 120 that comprises a water-soluble film and encapsulates the enzymatic detergent composition. Upon immersion in water, the enzymatic detergent composition is released from the first chamber into the water, typically in a period of 4 minutes or less, preferably 2 minutes or less.

The enzymatic detergent composition comprises one or more enzymes and, typically, additional ingredients as discussed further below. The enzymatic detergent composition may be in the form of a liquid, a gel, a powder, a liquid-gel mixture, a liquid-powder mixture, or a gel-powder mixture, among other possible forms.

In various embodiments, and with reference now to the schematic illustration of FIG. 2, the unit dose pack 100 of the present disclosure further comprises a second chamber 210 that is separate from the first chamber 110 and contains a water treatment composition. In some of these embodiments, the second chamber is formed from at least one second sheet of material 220 that comprises a water-soluble film and encapsulates the water treatment composition. The at least one second sheet of material 220 and the at least one first sheet of material 120 may be the same or different, for example, depending on the desired timing for release.

The water treatment composition may comprise, for example, a disinfectant, an anti-disinfectant, a water softener, a water hardener, an enzymatic catalyst, or other water-treating ingredients that support the cleaning function of the enzymatic detergent composition. Like the enzymatic detergent composition, the water treatment composition may be in the form of a liquid, a gel, a powder, a liquid-gel mixture, a liquid-powder mixture, or a gel-powder mixture, among other possible forms.

In some embodiments, the water treatment composition will depend upon the geographic destination of the unit dose packs. For example, where the geographic destination has hard water, the water treatment composition may comprise a water softener, where the geographic destination has soft water, the water treatment composition may comprise a water hardener, where the geographic destination has water with a high chlorine content, the water treatment composition may comprise a dechlorination agent, where the geographic destination has water with high or low pH, the water treatment composition may comprise a pH adjusting agent, where the geographic destination has water with elevated salinity, the water treatment composition may comprise a salinity reducing agent, and/or where the geographic destination has water with elevated ammonia or organic amines, the water treatment composition may comprise agents to remove or neutralize the same.

In some embodiments, where the unit dose pack comprises a water-treatment-composition-containing second chamber that is separate from the enzymatic-detergent-composition-containing first chamber, the water treatment composition may be released from the second chamber of the unit dose pack prior to release of the enzymatic detergent composition from the first chamber of the unit dose pack.

In some embodiments, and with reference now to the schematic illustration of FIG. 3, the unit dose pack 100 of the present disclosure further comprises a third chamber 310 that is separate from the first chamber 110 and the second chamber 210 and contains an additional treatment composition. In these embodiments, the third chamber may be formed from at least one third sheet of material 320 that comprises a water-soluble film and encapsulates the additional treatment composition. The at least one first sheet of material 120, the at least one second sheet of material 220, and the at least one third sheet of material 220 may be the same or different, for example, depending on the desired timing for release.

The additional treatment composition may comprise, for example, a disinfectant, an anti-disinfectant, a water softener, a water hardener, a dechlorination agent, a pH adjusting agent, a salinity reducing agent, and/or a agents to remove or neutralize ammonia or organic amines, among other ingredients. Like the enzymatic detergent composition and the water treatment composition, the additional treatment composition may be in the form of a liquid, a gel, a powder, a liquid-gel mixture, a liquid-powder mixture, or a gel-powder mixture, among other possible forms.

In some embodiments, upon immersion in water, the water treatment composition is released from the second chamber prior to release of the additional treatment composition from the third chamber, and the additional treatment composition is released from the third chamber prior to release of the enzymatic detergent composition from the first chamber. In particular embodiments, the water treatment composition may be a disinfectant such as a chlorination agent, and the additional treatment composition may be an anti-disinfectant such as a dechlorination agent.

The water-soluble films that are used in the unit dose packs of the present disclosure (i.e., the water-soluble films that may be present in first, second, third, etc. sheets of material) can be formed using any suitable water-soluble film-forming material. In some embodiments, the water-soluble film is a water-soluble polymer film. In some embodiments, the water-soluble polymer film may comprise one or more of following: polyvinyl ethers (PVE), polyvinyl alcohol, polyvinyl pyrrolidine, polyalkylene oxides such as polyethylene oxide, polyacrylamides, polycarboxylic acids, such as polyacrylic acid, polymethacrylic acid, and salts thereof, polyvinyl acetate, polyaminoacids and salts thereof, polyamides, polyanhydrides, polysaccharides, including natural gum and film-forming cellulosic polymers such as cellulose ethers, cellulose esters, cellulose amides, methyl cellulose, and hydroxypropyl methyl cellulose, as well as copolymers of the foregoing.

In addition to a water-soluble film, in some embodiments, the first, second, third, etc. sheet of material can comprise a water-resistant barrier layer disposed between the water-soluble polymer film and the encapsulated composition (e.g., enzymatic detergent composition, water treatment composition, additional treatment composition, etc.).

Figure 4:
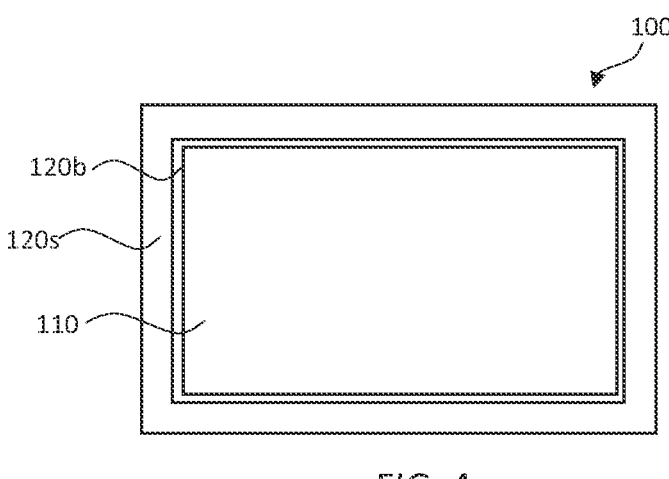
FIG. 4 schematically depicts a unit dose pack, in accordance with yet another embodiment of the present disclosure.

One embodiment of such a structure is shown in the schematic illustration of FIG. 4, which illustrates a unit dose pack 100 having a first chamber 110 that contains an enzymatic detergent composition, wherein the first chamber 110 is formed from at least one first sheet of material that comprises a water-soluble film 120s and water-resistant barrier layer 120b, which encapsulate the enzymatic detergent composition.

Examples of such a water-resistant barrier layers include various water-insoluble polymers, including silicones or other natural rubbers, and hydrophobic coating layers, among others.

A thickness of the water-resistant barrier layer may be very thin, such that when the water-soluble polymer film dissolves, the water-resistant barrier layer immediately tears, even with gentle agitation, releasing the enzymatic detergent composition. The thickness of the water-soluble polymer film may be, for example, at least 10 times, at least 25 times, at least 50 times, at least 100 times, or more, the thickness of the water-resistant barrier layer.

In some embodiments, at least one layer (e.g. a water-soluble polymer film layer) of the sheets of material that encapsulate the compositions described herein (e.g., enzymatic detergent composition, water treatment composition, additional treatment composition, etc.) may comprise a thermoplastic polymer such that the compositions can be encapsulated by a thermal process such as a heat-sealing process, among other possibilities.

In multi-chamber embodiments (e.g., embodiments having two chambers, three chambers, etc.), the chambers may have the same volume. In multi-chamber embodiments, the chambers may have the different volumes. For example, the first chamber may have a volume that ranges from 1.25 times to 1.5 times to 2 times to 5 times (or more) the volume of the second chamber. Or the first chamber may have a volume that ranges from 0.75 times to 0.5 times to 0.2 times (or less) the volume of the second chamber. Similarly, the second chamber may have a volume that ranges from 1.25 times to 1.5 times to 2 times to 5 times (or more) the volume of the third chamber. Or the second chamber may have a volume that ranges from 0.75 times to 0.5 times to 0.2 times (or less) the volume of the third chamber.

In multi-chamber embodiments, the encapsulated compositions (e.g., encapsulated enzymatic detergent composition, encapsulated water treatment composition, encapsulated additional treatment composition, etc.) may have the same color or may be of differing colors.

Where it is desired to release all of the compositions (e.g., enzymatic detergent composition, water treatment composition, additional treatment composition, etc.) at once, the sheets of material (e.g., the first, second, third, etc. sheets of material) encapsulating the compositions may be the same.

In multi-chamber embodiments, where it is desired stagger the release of the compositions (e.g., enzymatic detergent composition, water treatment composition, additional treatment composition, etc.), the sheets of material encapsulating the compositions will be different.

In some of these embodiments, the sheets of material may be formed using the same water-soluble film material; however, the thickness of the water-soluble films will vary, with thinner water-soluble films being used for earlier release and thicker water-soluble films being used for later release.

In some of these embodiments, the sheets of material may be formed using different water-soluble film materials. For example, water-soluble films containing polymers with higher water solubility may be used for earlier release and water-soluble films containing polymers with lower water solubility may be used for later release. As another example, because higher molecular weight polymers generally have lower water solubility than lower molecular weight polymers of the same composition, water-soluble films containing polymers with lower molecular weight may be used for earlier release and water-soluble films containing polymers with higher molecular weight may be used for later release.

A range of enzymatic detergent compositions may be used in conjunction with the unit dose pack of the present disclosure. The enzymatic detergent compositions comprise one or more enzymes. Beneficial enzymes include, amylases, proteases, cellulases, lipases, and combinations of the same.

Any suitable amylase or mixture of amylases, from any source, can be used in the enzymatic detergent compositions. For example, the amylase enzymes can be derived from a plant, an animal, or a microorganism such as a yeast, a mold, or a bacterium. Beneficial amylase enzymes include, but are not limited to, those derived from a *Bacillus*, such as *B. licheniformis, B. amyloliquefaciens, B. subtilis*, or *B. stearothermophilus*. The amylase can be purified or a component of a microbial extract, and either wild type or variant (either chemical or recombinant).

Any suitable protease or mixture of proteases, from any source, can be used in the enzymatic detergent compositions. For example, the protease enzymes can be derived from a plant, an animal, or a microorganism such as a yeast, a mold, or a bacterium. Beneficial protease enzymes include, but are not limited to, the enzymes derived from *Bacillus subtilis, Bacillus licheniformis* and *Streptomyces griseus*. The protease can be purified or a component of a microbial extract, and either wild type or variant (either chemical or recombinant).

Any suitable cellulase or mixture of cellulases, from any source, can be used in the enzymatic detergent compositions. For example, the cellulase enzymes can be derived from a plant, an animal, or a microorganism such as a fungus or a bacterium. The cellulase can be purified or a component of a microbial extract, and either wild type or variant (either chemical or recombinant).

Any suitable lipase or mixture of lipases, from any source, can be used in the enzymatic detergent compositions. For example, the lipase enzymes can be derived from a plant, an animal, or a microorganism such as a fungus or a bacterium. The lipase can be purified or a component of a microbial extract, and either wild type or variant (either chemical or recombinant).

The enzymatic detergent compositions can comprise additional enzymes in addition to the foregoing. Additional enzymes may include, but are not limited to, cutinases, peroxidases, gluconases, or mixtures thereof.

In addition to one or more enzymes, the enzymatic detergent compositions may comprise a number of other ingredients, including one or more of the following: stabilizers such as polyols (e.g., C3-C8 polyols such as glycerin, etc.), preservatives such as isothiazolinones (e.g., methylisothiazolinone, benzisothiazolinone, etc.), buffers and/or alkalinity sources, corrosion inhibitors, surfactants, defoamers, dyes, fragrances, water conditioning agents, and combinations thereof.

In multi-chamber embodiments, the water treatment composition and additional treatment composition may contain variety of ingredients selected from, for example, from one or more disinfectants such as chlorine, chloramine, one or more anti-disinfectants, for instance, dechlorinators such as sodium thiosulfate or sodium bisulfate, one or more water softeners, for example, polycarboxylic acid polymers, phosphates, chelators such as citric acid, EDTA, sodium phytate, tetrasodium glutamate diacetate, or trisodium ethylenediamine disuccinate, one or more water hardeners including calcium salts and magnesium salts, one or more acidifying agents, for instance, citric acid, fumaric acid, hydrochloric acid, lactic acid, malic acid, nitric acid, phosphoric acid, propionic acid, sodium phosphate monobasic, sulfuric acid, or tartaric acid, and/or one or more alkalizing agents, for instance, ammonium carbonate, diethanolamine, monoethanolamine, potassium hydroxide, sodium bicarbonate, sodium borate, sodium carbonate, sodium hydroxide, or trolamine, among others.

Although the term endoscope has been used hereinabove, it will be appreciated that various devices, including, but not limited to, duodenoscopes, colonoscopes, ureteroscopes, bronchoscopes, laparoscopes, sheaths, catheters, or any other suitable delivery device or medical device may be used in connection with this disclosure.

The invention claimed is:

1. A unit dose pack for forming a bath for cleaning medical instruments, the unit dose pack comprising at least a first chamber that contains an enzymatic detergent composition comprising one or more enzymes, the first chamber being formed from at least one first sheet of material that comprises a water-soluble film, and the at least one first sheet of material encapsulating the enzymatic detergent composition, wherein upon immersion in water, the enzymatic detergent composition is released from the first chamber into the water, wherein the first sheet of material further comprises a water-resistant barrier layer disposed between the water-soluble film and the enzymatic detergent composition.

2. The unit dose pack of claim 1, wherein the enzymatic detergent composition is a liquid composition, a gel composition, a powder composition, or a combination thereof.

3. The unit dose pack of claim 1, wherein the enzymatic detergent composition comprises a protease enzyme and/or an amylase enzyme.

4. The unit dose pack of claim 1, wherein the water-soluble film is a water-soluble polymer film.

5. The unit dose pack of claim 4, wherein the water-soluble polymer film is a polyvinyl ether film.

6. The unit dose pack of claim 1, wherein the water-resistant barrier layer is sufficiently thin such that after the water-soluble film dissolves upon immersion in water, the water-resistant barrier layer tears with agitation thereby releasing the enzymatic detergent composition.

7. The unit dose pack of claim 1, further comprising a second chamber that is separate from the first chamber and contains a water treatment composition, the second chamber being formed from at least one second sheet of material that comprises a water-soluble film, the at least one second sheet of material encapsulating the water treatment composition.

8. The unit dose pack of claim 7, wherein the at least one first sheet of material and the at least one second sheet of material are the same and wherein upon immersion in water the enzymatic detergent composition and the water treatment composition are released at substantially the same time.

9. The unit dose pack of claim 7, wherein the at least one first sheet of material and the at least one second sheet of material are different and wherein upon immersion in water the water treatment composition is released before the enzymatic detergent composition.

10. The unit dose pack of claim 9, wherein a thickness of the water-soluble film in the at least one first sheet of material is greater than a thickness of the water-soluble film in the at least one second sheet of material.

11. The unit dose pack of claim 9, wherein the water-soluble film in the at least one second sheet of material has a greater water solubility than a water solubility of the water-soluble film in the at least one first sheet of material.

12. The unit dose pack of claim 7, wherein the water treatment composition is selected from a disinfectant, an anti-disinfectant, a water softener, a water hardener, or a pH modifier.

13. The unit dose pack of claim 7, further comprising a third chamber that is separate from the first chamber and the second chamber, wherein the third chamber contains an additional treatment composition, the third chamber being formed from at least one third sheet of material that comprises a water-soluble film, the at least one third sheet of material encapsulating the additional treatment composition.

14. The unit dose pack of claim 13, wherein the water treatment composition is a water disinfectant composition, wherein the additional treatment composition is an anti-disinfectant composition, and wherein upon immersion in water, the water treatment composition is released prior to the additional treatment composition, and the additional treatment composition is released prior to release of the enzymatic detergent composition.

15. An article comprising a unit dose pack for forming a bath for cleaning medical instruments, the unit dose pack comprising (a) a first chamber that contains an enzymatic detergent composition that comprises a protease enzyme and amylase enzyme, the first chamber being formed from at least one first sheet of material that comprises a water-soluble polymer film, the at least one first sheet of material encapsulating the enzymatic detergent composition and (b) a second chamber that is separate from the first chamber and contains a water treatment composition, the second chamber being formed from at least one second sheet of material that comprises a water-soluble polymer film, the at least one second sheet of material encapsulating the water treatment composition, wherein the at least one first sheet of material further comprises a water-resistant barrier layer disposed between the water-soluble polymer film and the enzymatic detergent composition.

16. The article of claim 15, wherein the at least one first sheet of material and the at least one second sheet of material are different and wherein upon immersion in water the water treatment composition is released before the enzymatic detergent composition.

17. The article of claim 16, wherein a thickness of the water-soluble polymer film in the at least one first sheet of material is greater than a thickness of the water-soluble polymer film in the at least one second sheet of material.

18. The article of claim 15, wherein the water treatment composition is one of a water disinfectant and a water anti-disinfectant.

\* \* \* \* \*